US00PP30924P3

(12) United States Plant Patent
Austin

(10) Patent No.: US PP30,924 P3
(45) Date of Patent: Oct. 8, 2019

(54) ***ROSA HYBRIDA* SHRUB NAMED 'AUSPIKE'**

(50) Latin Name: *Rosa hybrida*
Varietal Denomination: AUSpike

(71) Applicant: David Austin Roses Ltd., Albrighton, Wolverhampton (GB)

(72) Inventor: David J. C. Austin, Wolverhampton (GB)

(73) Assignee: David Austin Roses Ltd., Albrighton (GB)

( * ) Notice: Subject to any disclaimer, the term of this patent is extended or adjusted under 35 U.S.C. 154(b) by 0 days.

(21) Appl. No.: 15/932,841

(22) Filed: May 3, 2018

(65) Prior Publication Data

US 2019/0098812 P1 Mar. 28, 2019

(30) Foreign Application Priority Data

Sep. 26, 2017 (GB) ..... PBR 5/2135
Oct. 3, 2017 (QZ) ..... PBR 2017/2475

(51) Int. Cl.
*A01H 5/02* (2018.01)
*A01H 6/74* (2018.01)

(52) U.S. Cl.
USPC ..... Plt./107
CPC ..... *A01H 6/749* (2018.05)

(58) Field of Classification Search
USPC ..... Plt./107
See application file for complete search history.

*Primary Examiner* — Anne Marie Grunberg
(74) *Attorney, Agent, or Firm* — KPPB LLP

(57) ABSTRACT

A variety of rose plant of the shrub class, named 'AUSpike'. The 'AUSpike' is a variety of a rose shrub with blooms of the deepest cerise pink, with numerous petals forming perfect large rosettes, each with a central button eye and a medium strength, fruity fragrance.

1 Drawing Sheet

Classification: The present invention relates to a new *Rosa hybrida* shrub of the market class 'English Rose'.

Variety denomination: The new plant has the varietal denomination 'AUSpike'.

CROSS-REFERENCE TO RELATED APPLICATION

The present application claims priority to UK Plant Patent No. 5/2135, filed Sep. 26, 2017, and European CPVO 2017/2475, filed Oct. 3, 2017.

ORIGIN OF INVENTION

This invention relates to a new and distinct variety of shrub rose plant named 'AUSpike', which was originated from the cross-pollination of the two 'unnamed' and unpatented seedlings of *Rosa hybrida.*

BACKGROUND OF THE INVENTION

The primary objective of this breeding was to produce a rose variety with blooms of the deepest cerise pink, with numerous petals forming perfect large rosettes, each with a central button eye and a medium strength, fruity fragrance, and that flowers prolifically over a long season with blooms that are not affected by bad weather.

SUMMARY OF THE INVENTION

Among the features which distinguish the new variety from others presently available and commercial rose cultivars known to the inventor is the following combination of characteristics: large, robust blooms with button eyes and many petals.

Asexual reproduction of the new variety by budding as performed at Bowling Green Lane in Albrighton, Britain shows that the foregoing and other distinguishing characteristics come true to form and are established and transmitted through succeeding asexual propagations. 'AUSpike' may be asexually propagated by budding. The budding successfully occurred on the plant/rootstock *Rosa* 'Dr. Huey' in the US and *Rosa dumetorum* in the UK for the observed plants.

COMPARISON WITH PARENTS

The maternal and paternal parents of 'AUSpike' are two unnamed seedlings. The new rose may be distinguished from its maternal parent, by the following combination of characteristics: the maternal parent is a lighter pink with smaller, deeply-cupped blooms. The new rose may be distinguished from its pollen parent, by the following combination of characteristics: the paternal parent has semi-double flowers.

COMPARISON WITH THE CLOSEST COMMERCIALLY AVAILABLE CULTIVAR

The closest commercially available cultivars to the new variety are the 'AUSkitchen' (U.S. Plant Pat. No. 23,099) and 'AUSvibrant' (U.S. Plant Pat. No. 20,960). The new rose may be distinguished from the 'AUSkitchen' based on the fact that Auskitchen has pyramidal clusters of 4 to 14 blooms, whereas 'AUSpike' has blooms held either singly or in a small cluster of 2 to 4 blooms. Moreover, neither 'AUSkitchen' nor 'AUSvibrant' has a button eye. In addition, 'AUSvibrant' has blooms that are larger and deeper than 'AUSpike' and has fewer prickles.

BRIEF DESCRIPTION OF ILLUSTRATION

The accompanying photograph illustrates the new variety and shows the flowering thereof from bud to full bloom depicted in color as nearly correct as it is possible to make in a color illustration of the character.

Throughout this specification, color references and/or values are based upon the Colour Chart of The Royal Horticultural Society (2001) except where common terms of color definition are employed.

DESCRIPTION OF THE NEW VARIETY

Observations of budded 'AUSpike' specimens were made at the nursery at David Austin Roses Limited in Albrighton, Wolverhampton, United Kingdom. The following description is of 1 year-old rose plants of the new variety grown in a garden environment in Albrighton, Britain in the month of June. Phenotypic expression may vary with environmental, cultural and climatic conditions, as well as differences in conditions of light and soil.

FLOWER CHARACTERISTICS

Blooming habit: Recurrent. The number of blooms per plant during the growing season is profuse, but there are too many to count.

Bud:

*Size*.—About 2 cm long and 1.8 cm in diameter when the petals start to unfurl.

*Form*.—The bud form is pointed ovoid.

*Color*.—When sepals first divide, the bud color is RHS 60A (red-purple group). When half blown, the upper sides of the petals are RHS 61C (red-purple group), and the lower sides of the petals RHS 61C (red-purple group).

*Calyx*.—Shape: opens to a star shape, with the sepals finally folding back against the penduncle. Length: 6.5 cm. Diameter: 6.5 cm.

*Sepals*.—Arrangement: Regularly arranged. Color: Upper Surface: RHS 138B (green group). Lower Surface: RHS 144A (yellow-green group). Length: 2.5 cm. Width: 6 mm. Shape: Lanceolate. Surface texture: Upper Surface: Downy. Lower Surface: Smooth. Number: There are no appendaged sepals, and 5 unappendaged sepals with hairy edges. The Sepal extensions are medium.

*Receptacles*.—Color: RHS N144A (yellow-green group). Shape: Apple. Size: Broad, about 11 mm long×12 mm wide. Surface: Smooth.

*Peduncle*.—Length: Medium, averaging about 7 cm. Surface: Glandular. Color: RHS N144A (yellow-green group). Strength: Strong.

Blooms:

*Size*.—Large, average open diameter is about 9 cm.

*Borne*.—Mostly singly with 1 to 4 blooms together in an inflorescence having a rounded shape.

*Stems*.—Strength: Strong, average length is about 7 cm. Diameter: 2 mm.

*Form*.—When first open, bloom is cupped.

*Permanence of bloom*.—Retains its form to the end.

*Type*.—Double.

Petalage: Number of petals under normal conditions: 90.

*Color*.—The upper sides of the petals are RHS N66B (red-purple group). The reverse sides of the petals are RHS 67C (red-purple group). The base of the petals has a spot that is RHS 5C (yellow group).

*Variegations*.—None.

*Discoloration*.—The general tonality at the end of the first day is RHS N66B (red-purple group), and at the end of the third day is RHS N66B (red-purple group).

*Fragrance*.—Moderate. Character of fragrance: Fruity.

Petals:

*Texture*.—Smooth.

*Size*.—Width: 2-4 cm. Length: 4 cm.

*Surface*.—Smooth.

*Shape*.—Obovate.

*Margin*.—Entire.

*Apex shape*.—Rounded.

*Base shape*.—Acute.

*Form*.—Tips slightly recurved and many petals folded vertically.

*Arrangement*.—Regularly arranged.

*Petaloids*.—Number: Around 8-20. Color: RHS N66B (red-purple group). Length: between 0.8-2 cm. Width: between 0.4-1 cm. Shape: Various shapes of deformed petal. Margin: Irregular.

*Persistence*.—Petals drop off cleanly before drying.

*Lastingness*.—On the plant: Fair. As a cut flower: not tested.

Reproductive parts:

*Stamens*.—Number: between 4-8. Length: 5 mm.

*Anthers*.—Length: 1.5 mm. Color: RHS 5A (yellow group). Arrangement: Mixed with petaloids.

*Filaments*.—Color: RHS 5A (yellow group). Length: 4 mm.

*Pollen*.—Color: RHS 14A (yellow-orange group). Amount: Scarce.

*Pistils*.—Number: approximately 10. Length: 6 mm.

*Styles*.—Color: RHS 151D (yellow-green group). Length: 5.2 mm.

*Stigmas*.—Color: RHS 151C (yellow-green group). Length: 0.4 mm.

*Hips*.—NONE Observed.

PLANT CHARACTERISTICS

Plant form: Shrub.

Plant growth: Vigorous.

Age to maturity: 2 years.

Mature plant: Height: 1 m 20 cm. Width: 60 cm.

Rootstock: 'Dr Huey' in the US and *Rosa dumetorum* 'Laxa' for the observed plants in the UK. Neither rootstock is patented in the US.

Foliage:

*Number*.—Leaflets on normal mid-stem leaves is: 5 (some) and 7 (some) (including terminal leaflet).

*Size*.—Medium, about 15 cm long×12 cm wide.

*Quantity*.—Abundant. Number of leaves per flowering stem is: 10.

*Color*.—New foliage: Upper side: RHS 146A (yellow-green group) tinged with RHS 184A (greyed-purple group). Lower side: RHS 184A (greyed-purple group). Old foliage: Upper side: RHS 147A (yellow-green group). Lower side: RHS 147B (yellow-green group).

Leaflets:

*Size*.—About 7 cm long×4.8 cm wide.

*Shape*.—Pointed oval.

*Base shape*.—Cordate.

*Apex shape*.—Acuminate.

*Texture*.—Leathery.

*Glossiness*.—Medium.

*Edge*.—Serrated.

*Serrations*.—Double.

*Petiole*.—Color: RHS 146A (yellow-green group). Length: 5 cm. Width: 2 mm. Surface Texture: Slightly glandular with an occasional very small prickle.

*Petiole rachis*.—Color: RHS 146A (yellow-green group). Underside: glandular with an occasional very small prickle.

*Stipules*.—Length: 2.8 cm, glandular. Color: RHS 146A (yellow-green group).

*Auricle*.—Shape: Lanceolate. Length: 8 mm. Width: 1.5 mm. Color: RHS 146A (yellow-green group).

*Vein color*.—Color: Upper side: RHS 147A (yellow-green group), Lower side: RHS 147B (yellow-green group).

*Venation pattern*.—Reticulate.

Wood:

*New wood*.—Color: RHS 144A (yellow-green group). Bark: Smooth.

*Old wood*.—Color: RHS 144A (yellow-green group). Bark: Smooth (with prickles).

Branching habit:

*Number of lateral branches*.—6.

*Lateral branch dimensions*.—Length: 50 cm. Diameter: 6 mm.

Stems:

*Mature stem*.—Length: 50 cm. Diameter: 6 mm.

*Internode distance*.—7 cm. The above measurements are all variable, depending on growing conditions in a season.

*Stem pubescence present*.—No.

Prickles:

*Quantity*.—On main canes from base: Ordinary. Number per stem length: 10 per 10 cm. On laterals from main canes: Ordinary. Number per stem length: 10 per 10 cm.

*Form*.—Deep concave.

*Length*.—6-7 mm.

*Color when young*.—RHS 184B (greyed-purple group).

*Color when mature*.—RHS 184D (greyed-purple group).

Small prickles:

*Quantity*.—Main stalk: Many. Number per stem length: 20 per 10 cm. Laterals: Many. Number per stem length: 20 per 10 cm.

*Color*.—When young: RHS 184B (greyed-purple group). When mature: RHS 184D (greyed-purple group).

Disease resistance:

*Powdery mildew* (*Podosphaera pannosa*).—Resistant.

*Downy mildew* (*Peronospora species*).—Resistant.

*Blackspot* (*Diplocarpon rosae*).—Resistant.

*Rust* (*Phragmidium tuberculatum*).—Resistant.

Pest resistance: Not tested.

Winter hardiness: Not tested.

Growing conditions: Normal garden conditions.

What is claimed is:

1. A new and distinct variety of rose plant of the shrub class, substantially as herein shown and described.

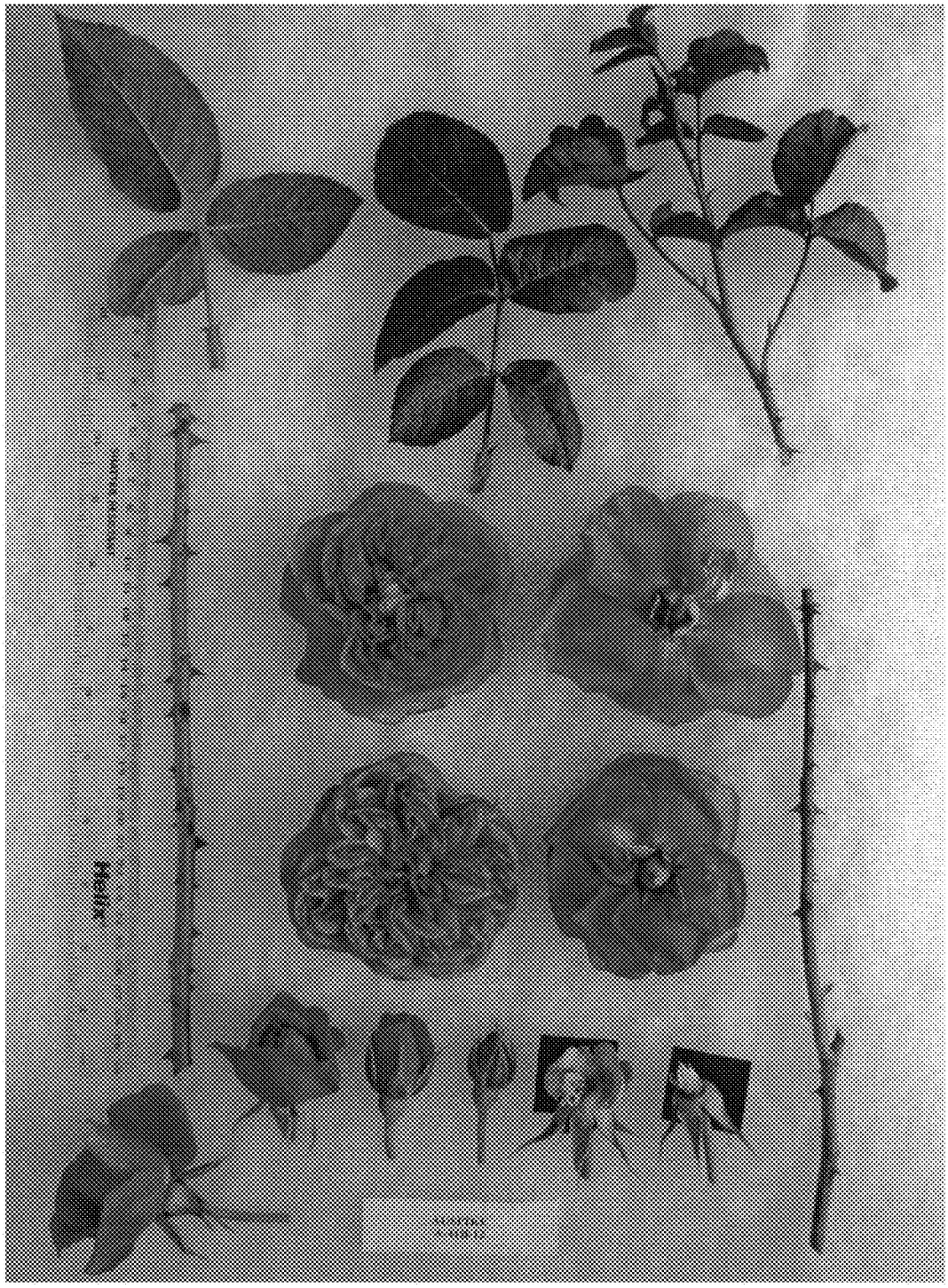

* * * * *